United States Patent [19]
Kobayashi et al.

[11] Patent Number: 5,824,414
[45] Date of Patent: Oct. 20, 1998

[54] PREPARATION OF SPHERICAL POLYPHENOL PARTICLES

[75] Inventors: Shiro Kobayashi; Hiroshi Uyama, both of Miyagi-ken; Sunao Maeda, Aichi-ken; Shinichirou Tawaki, Kanagawa-ken, all of Japan

[73] Assignees: Mitsui Chemicals, Inc., Tokyo; Shiro Kobayashi, Miyagi-ken, both of Japan

[21] Appl. No.: 633,378

[22] Filed: Apr. 17, 1996

[30] Foreign Application Priority Data

Apr. 28, 1995 [JP] Japan .................................. 7-105380

[51] Int. Cl.$^6$ ....................................................... C12P 1/00
[52] U.S. Cl. ........................... 428/402; 435/41; 528/206; 528/210; 528/212
[58] Field of Search ................................. 435/41; 428/402; 528/206, 210, 212

[56] References Cited

U.S. PATENT DOCUMENTS

| | | | |
|---|---|---|---|
| 5,153,298 | 10/1992 | Pokora et al. | 528/86 |
| 5,324,436 | 6/1994 | John et al. | 210/638 |

FOREIGN PATENT DOCUMENTS

| | | |
|---|---|---|
| 0126394 | 11/1984 | European Pat. Off. . |
| WO87/02939 | 5/1987 | WIPO . |

OTHER PUBLICATIONS

Polymer Preprints, vol. 44, No. 2, 17–19, Sep. 1995, Japan, p. e584 XP000600323, H. Kurioka et al, "Preparation of Polyphenol Particles by Enzymatic Oxidative Polymerization".

Chemistry Letters, No. 9, Sep. 1995, Japan, pp. 795–796, XP002013414, H. Uyama et al, "Preparation of Polyphenol Particles by Dispersion Polymerization Using Enzyme as Catalyst" *Abstract*.

Ma Lin et al, Transaction of Chinese Patent CN 1091141A, Oct. 1993.

*Primary Examiner*—Jeffrey C. Mullis
*Attorney, Agent, or Firm*—Burns, Doane, Swecker & Mathis, L.L.P.

[57] ABSTRACT

Phenols are reacted with hydrogen peroxide in a solution comprising an organic solvent compatible with water, water, a peroxidase and a dispersing agent to obtain spherical polyphenol particles.

12 Claims, 3 Drawing Sheets

1μm

1μm

Comparative

1μm

Comparative

PREPARATION OF SPHERICAL POLYPHENOL PARTICLES

BACKGROUND OF THE INVENTION

1. Field of the Invention

The present invention relates to a process for preparing spherical polyphenol particles. Particularly it relates to a process for preparing spherical polyphenol particles by using a dispersing agent.

2. Prior Art

Few processes for preparing spherical polyphenol particles without methylene chains have been found and only one example described below is shown. The example is a process for preparing spherical polyphenol particles in a reversed micelle polymerization system (Polymeric Materials: Science and Engineering Preprint, American Chemical Society, 68, 171–172(1993)).

This process, however, has a few problems. First, the monomer concentration is low, and there are great difficulties in commercially producing a spherical polyphenol particle. An emulsifier (anionic surfactant) of 3 moles or above per mole of the monomer is needed to obtain a spherical resin. The amount is 10 or well over in terms of ratio by weight. Removing the remaining emulsifier requires a lot of labor. Second, a reaction solvent consisting of water and an organic solvent, especially a reaction solvent with a significant amount of water is a double-layer system and the formation of particles is not found in it. Additionally, only p-ethylphenol is used to carry out these tests. Furthermore, these p-ethylphenol molecules link up with each other at positions ortho to the hydroxyl group. This reaction mechanism is shown as follows. A mixture consisting of isooctane, an anionic surfactant and a buffer solution is mixed to form micelles. A buffer solution in which an enzyme is soluble is added to form micelles containing the enzyme. A hydrogen peroxide aqueous solution is added to cause polymerization in the surface of the micelles and polymer particles grow up in the micelles.

JP-B-6-68017 (Tokkohei), U.S. Pat. No. 4,647,952, discloses that a phenolic resin is prepared by reacting a phenol with a peroxide and a peroxidase or an oxidase enzyme in an organic solvent, a mixture consisting of ethanol or ethyl acetate and a potassium phosphate buffer solution. Neither surfactants nor dispersing agents are used in the reaction. The present inventors found that the thus-obtained polymer particles were amorphous.

JP-A-4-110093 (Tokkaihei) discloses a wastewater treatment technology. This is a process for removing polyphenols in an aqueous solution. A hydrophilic polymer is added to prevent the intended product from being caught in an enzyme and then keep the activity of the enzyme. The reaction is carried out in an aqueous solution and the limiting concentration of a substrate is about 50 g/l, when phenol itself is used as the substrate. The limiting concentration is further reduced when alkylated phenols are used. This reaction, therefore, is absolutely unavailable in synthesis of polymers.

The above-mentioned processes are neither general nor equal to the commercial production of spherical polyphenol particles.

SUMMARY OF THE INVENTION

The present inventors earnestly studied to solve the above-mentioned problems and found a process for adding a dispersing agent to selectively prepare spherical polyphenol particles having optional diameters without forming micelles.

A general object of the present invention is to provide a process for preparing a spherical polyphenol particle which comprises preparing a solution comprising a phenol, an organic solvent, water, a peroxidase and a dispersing agent, adding hydrogen peroxide into the solution to obtain a reaction mixture and separating the spherical polyphenol particle from the reaction mixture.

Polymer emulsions of spherical polyphenol particles prepared according to the present invention have low viscosity (improvement of work efficiency). These particles are expected to be available in the field of dyestuffs. Concrete examples include a packing material for high performance liquid chromatography (HPLC) which uses its phenolic hydroxyl groups and a spacer for uniform space. Graphite beads, prepared by incinerating these particles, are expected to be suitable for adsorbents or lightweight particles.

DESCRIPTION OF THE PREFERRED EMBODIMENT

Figure 1:
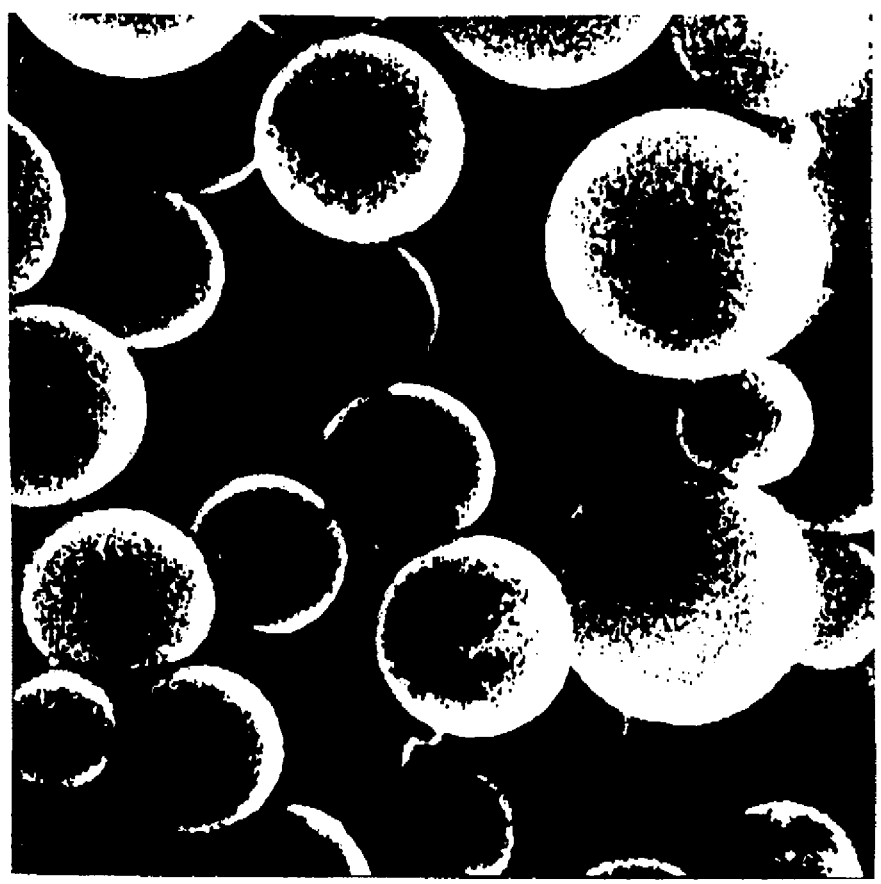
FIG. 1 is a scanning electron microscope photograph of a spherical particle obtained by the process of Example 4.

Phenols are illustrated according to the formula (1).

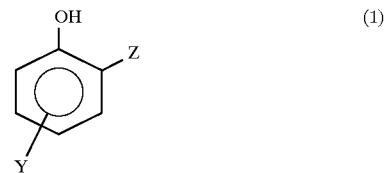

wherein Y and Z each are a hydrogen atom, a halogen atom, an alkyl group, an alkoxy group, an allyl group, an aryl group, a phenylalkyl group, a carboxyl group of the formula —COOR where R is a hydrogen atom or a lower alkyl group of 1 to 5 carbon atoms or an amino group of the formula —NR$^1$R$^2$ where R$^1$ and R$^2$ each are a hydrogen atom, a lower alkyl group of 1 to 5 carbon atoms or a phenylalkyl group, Z in conjunction with the adjacent meta position may form a condensed benzene ring, and Y or Z is a hydrogen atom when Y is present at a position ortho or para to the hydroxyl group.

Alkyl groups illustrated by Y or Z include alkyl groups containing at most 10 carbon atoms such as t-butyl, n-butyl, octyl and nonyl. The number of carbon atoms is 1 to 10 when Y or Z is an alkoxy group. Typical examples are phenyl itself or substituted phenyl groups with a halogen atom, a hydroxyl group or a lower alkyl group when Y or Z is an aryl group. The halogen atom is fluorine, chlorine, bromine or iodine. The phenols include 4-t-butylphenol, 4-n-butylphenol, 4-ethylphenol, cresol, p-phenylphenol, p-octylphenol, p-hydroxybenzoic acid, 4-hydroxynaphthoic acid, p,p'-biphenol, 4-aminosalicylic acid, salicylic acid, methyl salicylate, ethyl salicylate and ethyl 4-hydroxybenzoate. Phenol itself, p-phenylphenol and cresol are more preferred as phenols.

Bisphenols are illustrated according to the formula (2).

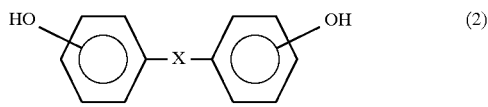

wherein X is —CO—, —(R$^1$)C(R$^2$)—, —S—, —O—, —SO$_2$—, —OR$^3$—, —R$^4$O—, —R$^5$— or —C(R$^6$), R$^1$ AND R$^2$ each are a hydrogen atom or a linear or chain alkyl group of 1 to 5 carbon atoms, R$^3$ and R$^4$ each are a linear or chain alkylene group of 1 to 5 carbon atoms, R$^5$ is a linear or chain alkylene group of 1 to 8 carbon atoms, and R$^6$ is an alkylene group of 2 to 5 carbon atoms and conjoins with its adjacent carbon atom in forming a saturated aliphatic cycle.

Particularly bisphenol F and bisphenol A which have hydroxyl groups at the p- and p'-positions of the benzene rings are preferred.

The reaction is carried out in a mixture of water and an organic solvent. The organic solvent is compatible with water. Preferable organic solvents include methanol, ethanol, 1,4-dioxane, tetrahydrofuran(THF), N,N-dimethylformamide(DMF), dimethylsulfoxide(DMSO), acetonitrile and acetone.

Distilled water or buffer solutions may be used as the water. The pH value is pH 4 to pH 12. Preferable buffer solutions include phosphate buffer solution, acetate buffer solution and succinate buffer solution. Preferably the mixing ratio by volume of the water to the organic solvent is 1:9 to 9:1.

Peroxidases are used as oxidative polymerization catalysts of phenols. The most preferred peroxidase is horseradish peroxidase or soybean peroxidase and may also be chloroperoxidase or lactoperoxidase. The amount of the above-mentioned peroxidases is usually 10 mg to 10 g per 100 g of a phenol as a substrate.

Two enzymes may be used in combination in a process of the present invention. One enzyme is used for oxidative polymerization and another enzyme, for dehydrogenation or generation of peroxides such as hydrogen peroxide. The enzyme for oxidative polymerization is the same as mentioned above and the enzyme for generation of hydrogen peroxide is an enzyme having oxidase activity. The most preferred oxidase is glucose oxidase. Alcohol oxidase, cholesterol oxidase, acyl coenzyme A oxidase (Acyl—CoA oxidase), choline oxidase and sarcosine oxidase may also be used.

Dispersing agents include alkylether type, alkylarylether type, alkylester type, polyoxyethylenealkylamine type, polyoxyethylenealkylamide type, polyoxyethylenepolyoxypropylene type, sorbitanalkylester type, fatty acid ethanolamide type and saccharoseester type. Particularly preferred examples are poly(methyl vinyl ether), poly(N-vinyl-2-pyrolidone), poly(oxyethylene), poly(2-ethyl-2-oxazoline), poly(vinyl alcohol), poly(acrylamide), hydroxyethyl cellulose and soluble starch. The amount is 1 to 100 parts by weight per 100 parts by weight of the raw material phenol and the preferred amount is 10 to 50 parts by weight per 100 parts by weight of the raw material phenol. The diameter of a spherical polyphenol particle depends on the amount of a dispersing agent. The diameter is decreased when the amount is large. The diameter is increased when the amount is small.

The reaction is carried out as follows. (1) An organic solvent is mixed with water to prepare a solution. A phenol, an enzyme and a dispersing agent are dissolved in the solution, followed by stirring. (2) On the other hand, a phenol is dissolved in an organic solvent and an enzyme is dissolved in water. Both solutions are mixed to prepare a solution and a dispersing agent is added into the solution, follow ed by stirring. The substrate concentration is usually 1 to 1,000 g per liter of the solvent.

Hydrogen peroxide is usually most preferred. A peroxide is dropped slowly to start the reaction. The amount of hydrogen peroxide is 0.1 to 2.0 moles per mole of the phenol. The reaction temperature is usually 0° to 45° C. Slow dropping is preferred because high concentrations of the peroxide in the reaction mixture restrain the reaction and deactivate the enzyme.

After completion of the reaction, polymers are separated with a centrifugal separator or a vacuum filter. A solution which has the same composition as the solution used in the reaction does may also be added into the thus-obtained polymer to wash by ultrasonic wave treatment. The intended spherical polyphenol particle is obtained according to the additional separation of the polymer with a centrifugal separator or a vacuum filter.

The particle diameter of the thus-prepared spherical polyphenol particle is determined with a scanning electron microscope(SEM). Generally spherical polyphenol particles do not decompose below about 350° C. according to the result of TGA analysis. About 40% of the polymer remains at 1,000° C. in nitrogen atmosphere according to the result of TGA analysis. The polymer completely decomposes at about 500° C. in air atmosphere according to the result of TGA analysis. No melting point of the polymer is found according to the result of DSC analysis.

The polymer is insoluble in ordinary solvents.

The present invention will be explained below in more detail by way of examples and comparative examples.

Example 1

A substrate of 0.47 g (5.0 mmole) of phenol, 0.12 g of poly(methyl vinyl ether) and 10 mg of horseradish peroxidase were dissolved in a mixed solution of 10 ml of potassium phosphate buffer solution (pH 7.0, 0.1 mole) and 15 ml of 1,4-dioxane. 30 wt. % hydrogen peroxide aqueous solution (28 μl) was dropped 20 times at 15-minute intervals at room temperature (about 20° C.), followed by stirring. The reaction mixture was transferred to a centrifugal tube 24 hours later and the polymer was separated by centrifugal force. The supernatant was removed. A mixed solution of distilled water and 1,4-dioxane (20:80 vol. %) was added into the polymer to again disperse the polymer by ultrasonic wave treatment. The polymer was again separated by centrifugal force and dried in a vacuum dryer to obtain 0.47 g of the polymer. The thus-obtained polymer was observed with a SEM (scanning electron microscope). The particles were spherical and the average diameter was about 250 nm.

Example 2

A substrate of 0.47 g (5.0 mmole) of phenol, 0.12 g of poly(oxyethylene) and 10 mg of horseradish peroxidase were dissolved in a mixed solution of 15 ml of distilled water and 10 ml of 1,4-dioxane. 30 wt. % hydrogen peroxide aqueous solution (28 μl) was dropped 20 times at 15-minute intervals at room temperature (about 20° C.), followed by stirring. The reaction mixture was transferred to a centrifugal tube 24 hours later and the polymer was separated by centrifugal force. The supernatant was removed. A mixed solution of distilled water and 1,4-dioxane (20:80 vol. %) was added into the polymer to again disperse the polymer by ultrasonic wave treatment. The polymer was again separated by centrifugal force and dried in a vacuum dryer to obtain 0.45 g of the polymer. The thus-obtained polymer was observed with a SEM (scanning electron microscope). The particles were spherical and the average diameter was about 500 nm.

Example 3

A substrate of 0.47 g (5.0 mmole) of phenol, 0.12 g of poly(oxyethylene) and 10 mg of horseradish peroxidase were dissolved in a mixed solution of 10 ml of potassium phosphate buffer solution (pH 7.0, 0.1 mole) and 15 ml of 1,4-dioxane. 30 wt. % hydrogen peroxide aqueous solution (28 µl) was dropped 20 times at 15-minute intervals at room temperature (about 20° C.), followed by stirring. The reaction mixture was transferred to a centrifugal tube 24 hours later and the polymer was separated by centrifugal force. The supernatant was removed. A mixed solution of distilled water and 1,4-dioxane (20:80 vol. %) was added into the polymer to again disperse the polymer by ultrasonic wave treatment. The polymer was again separated by centrifugal force and dried in a vacuum dryer to obtain 0.47 g of the polymer. The thus-obtained polymer was observed with a SEM (scanning electron microscope). The particles were spherical and the average diameter was about 300 nm.

Example 4

A substrate of 0.85 g (5.0 mmole) of p-phenylphenol, 0.12 g of poly(methyl vinyl ether) and 10 mg of horseradish peroxidase were dissolved in a mixed solution of 10 ml of potassium phosphate buffer solution (pH 7.0, 0.1 mole) and 15 ml of 1,4-dioxane. 30 wt. % hydrogen peroxide aqueous solution (28 µl) was dropped 20 times at 15-minute intervals at room temperature (about 20° C.), followed by stirring. The reaction mixture was transferred to a centrifugal tube 24 hours later and the polymer was separated by centrifugal force. The supernatant was removed. A mixed solution of distilled water and 1,4-dioxane (20:80 vol. %) was added into the polymer to again disperse the polymer by ultrasonic wave treatment. The polymer was again separated by centrifugal force and dried in a vacuum dryer to obtain 0.79 g of the polymer. The thus-obtained polymer was observed with a SEM (scanning electron microscope). The particles were spherical and the average diameter was about 300 nm as shown in FIG. 1.

Comparative Example 1

The same procedure as that in Example 1 was repeated except that the dispersing agent was not used. The yield was 0.47 g and 100%. The thus-obtained polymer was observed with a SEM (scanning electron microscope). The particles were amorphous and not spherical.

Comparative Example 2

Figure 2:
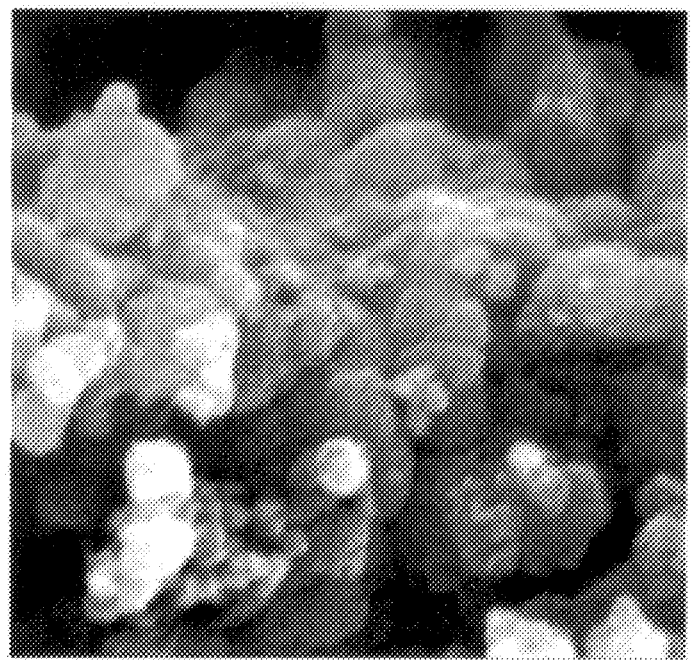
FIGS. 2 and 3 are also scanning electron microcope photographs of the products obtained by the polymerization processes of Comparative Examples 2 and 3, respectively.

The same procedure as that in Example 1 was repeated except that 0.12 g of polyethyleneimine as a cationic dispersant in place of the dispering agent. The thus-obtained polymer was observed with a SEM (scanning electron microscope). The particles were amorphous and not spherical as shown in FIG. 2.

Comparative Example 3

Figure 3:
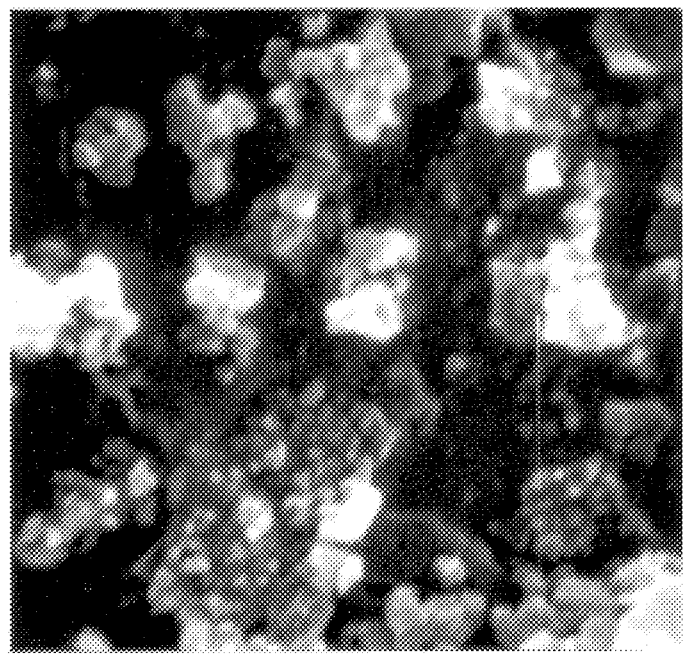

The same procedure as that in Example 1 was repeated except that 0.12 g of bis(2-ethylhexyl) sodium sulfosuccinate as an anionic surfactant in place of the dispersing agent. The thus-obtained polymer was observed with a SEM (scanning electron microscope). The particles were amorphous and not spherical as shown in FIG. 3.

What is claimed is:

1. A process for preparing a spherical polyphenol particle which comprises preparing a solution comprising a phenol, a water-miscible organic solvent, water, a peroxidase and a dispersing agent selected from the group consisting of poly(methyl vinyl ether), poly(N-vinyl-2-pyrrolidone), poly(oxyethylene), poly(2-ethyl-2-oxazoline), poly(vinyl alcohol), poly(acrylamide), hydroxyethyl cellulose and soluble starch, without forming micelles in the solution, adding hydrogen peroxide into the solution to obtain a reaction mixture and separating the spherical polyphenol particles from the reaction mixture.

2. A process according to claim 1, in which the phenol is represented by the formula (1),

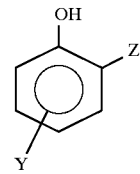

wherein Y and Z each are a hydrogen atom, a halogen atom, an alkyl group, an alkoxy group, an allyl group, an aryl group, a phenylalkyl group, a carboxyl group of the formula —COOR where R is a hydrogen atom or a lower alkyl group of 1 to 5 carbon atoms or an amino group of the formula —NR$^1$R$^2$ where R$^1$ and R$^2$ each are a hydrogen atom, a lower alkyl group of 1 to 5 carbon atoms or a phenylalkyl group, Z in conjunction with the adjacent meta position may form a condensed benzene ring, and Y or Z is a hydrogen atom when Y is present at a position ortho or para to the hydroxyl group.

3. A process according to claim 1, in which the phenol is Phenol, p-phenylphenol or cresol.

4. A process according to claim 1, in which the phenol is represented by the formula (2),

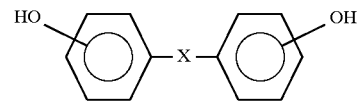

wherein X is —CO—, —(R$^1$)C(R$^2$)—, —S—, —O—, —SO—, —SO$_2$—, —OR$^3$—, R$^4$O—, —R$^5$— or —C(R$^6$)—, R$^1$ and R$^2$ each are a hydrogen atom or a linear or branched alkyl group of 1 to 5 carbon atoms, R$^3$ and R$^4$ each are a linear or chain alkylene group of 1 to 5 carbon atoms, R$^5$ is a linear or branched alkylene group of 1 to 8 carbon atoms, and R$^6$ is an alkylene group of 2 to 5 carbon atoms and conjoins with its adjacent carbon atom in forming a saturated aliphatic cycle.

5. A process according to claim 1, in which the phenol is bisphenol F or bisphenol A.

6. A process according to claim 1, in which the dispersing agent is poly(methyl vinyl ether) or poly(oxyethylene).

7. A process according to claim 1, in which the amount of the dispersing agent is 1 to 100 parts by weight per 100 parts by weight of the phenol.

8. A process according to claim 1, in which the mixing ratio by volume of the water to the organic solvent is 1:9 to 9:1.

9. A process according to claim 1, in which the organic solvent is selected from the group consisting of a lower alcohol, acetone, 1,4-dioxane and tetrahydrofuran.

10. A process according to claim 1, in which the water is distilled water or a buffer solution of pH 4 to pH 12.

11. A process according to claim 10, in which the buffer solution is potassium phosphate buffer solution, acetate buffer solution or succinate buffer solution.

12. A process according to claim 1, in which the peroxidase is horseradish peroxidase or soybean peroxidase.

* * * * *